(12) United States Patent
Grodzki et al.

(10) Patent No.: US 12,727,780 B2
(45) Date of Patent: Sep. 8, 2026

(54) RECORDING OF MAGNETIC RESONANCE DATA IN ORDER TO PREVENT CROPPING EFFECTS

(71) Applicant: Siemens Healthineers AG, Forchheim (DE)

(72) Inventors: David Grodzki, Erlangen (DE); Uvo Hölscher, Erlangen (DE)

(73) Assignee: Siemens Healthineers AG, Forchheim (DE)

(*) Notice: Subject to any disclaimer, the term of this patent is extended or adjusted under 35 U.S.C. 154(b) by 0 days.

(21) Appl. No.: 19/250,405

(22) Filed: Jun. 26, 2025

(65) Prior Publication Data

US 2026/0000314 A1 Jan. 1, 2026

(30) Foreign Application Priority Data

Jun. 28, 2024 (DE) ..................... 10 2024 206 085.2

(51) Int. Cl.

| | |
|---|---|
| ***A61B 5/055*** | (2006.01) |
| ***G06T 5/10*** | (2006.01) |
| ***G06T 5/80*** | (2024.01) |
| ***G06T 11/00*** | (2026.01) |
| ***G06T 12/20*** | (2026.01) |
| ***G16H 30/40*** | (2018.01) |

(52) U.S. Cl.

CPC ................ *A61B 5/055* (2013.01); *G06T 5/10* (2013.01); *G06T 5/80* (2024.01); *G06T 12/20* (2026.01); *G16H 30/40* (2018.01)

(58) Field of Classification Search

CPC .. A61B 5/055; G06T 5/10; G06T 5/80; G06T 12/20; G06T 11/00; G16H 30/40; G16H 50/20; G01R 33/543; G01R 33/56545; G01R 33/56563; G01R 33/56572

See application file for complete search history.

(56) References Cited

U.S. PATENT DOCUMENTS

| | | | | |
|---|---|---|---|---|
| 9,547,062 | B2 * | 1/2017 | Grodzki | ........... G01R 33/56572 |
| 2021/0173031 | A1 * | 6/2021 | Gras | .................... G01R 33/546 |

OTHER PUBLICATIONS

Dec. 10, 2025 (DE) English Translation of Decision to Grant—App. 102024206085.2.

(Continued)

*Primary Examiner* — Amal Aly Farag

(74) *Attorney, Agent, or Firm* — Banner & Witcoff, Ltd.

(57) ABSTRACT

Techniques are described for recording of magnetic resonance data to prevent cropping effects. A loss factor indicates an expected reduction of an image reconstructed on the basis of measurement data recorded using the loaded measurement protocol and determines filter parameters for a frequency filter for filtering frequencies of echo signals, received when recording measurement data with the measurement protocol, on the basis of the loss factor and on the basis of the desired field of view, and determines an oversampling factor on the basis of the filter parameters of the frequency filter. The oversampling factor specifies an oversampling to be applied when recording of measurement data. Oversampled measurement data is recorded using the determined filter parameters and the oversampling factor when implementing the loaded measurement protocol.

14 Claims, 3 Drawing Sheets

(56) References Cited

OTHER PUBLICATIONS

Jul. 16, 2025 (DE) English Translation of Office Action—App. 102024206085.2.
Jul. 16, 2025 (DE) Office Action—App. 102024206085.2.
Dec. 10, 2025 (DE) Decision to Grant—App. 102024206085.2.
Stadler Alfred et al: "Artifacts in Body MR Imaging: Their Appearance and How to Eliminate Them", European radiology; 2007; 17. Jg; Nr. 5; S. 1242-1255.

* cited by examiner 1
3
U
7.1
7.2
5
L
S1
S2
7
9
RF TX/RX controller
7'
Gradient controller
5'
13
Pulse sequence controller
S
15
Filter parameter-determining controller
Storage
26
I/O

RECORDING OF MAGNETIC RESONANCE DATA IN ORDER TO PREVENT CROPPING EFFECTS

CROSS-REFERENCE TO RELATED APPLICATIONS

The present application claims priority to and the benefit of Germany patent application no. DE 10 2024 206 085.2, filed on Jun. 28, 2024, the contents of which are incorporated herein by reference in their entirety.

TECHNICAL FIELD

The disclosure relates to improved recording of magnetic resonance data in order to prevent cropping effects.

BACKGROUND

The magnetic resonance (MR) technique is a known technique with which images of the inside of an examination object can be generated. Put simply, the examination object is positioned for this purpose in a magnetic resonance device in a comparatively strong static, homogeneous basic magnetic field, also called B0 field, with field strengths of 0.2 tesla to 7 tesla or more, so the nuclear spins thereof are oriented along the basic magnetic field. In order to trigger nuclear spin resonances which can be measured as signals, radio-frequency (RF) excitation pulses are irradiated into the examination object, the triggered nuclear spin resonances measured as what is known as k-space data by means of coils configured to receive and, on the basis of this, MR images are reconstructed or spectroscopy data is ascertained.

The magnetic alternating field generated by the excitation pulses irradiated by means of at least one transmit coil is also referred to as a B1 field. In order to spatially encode the measurement data, fast-switched magnetic gradient fields, called gradients for short, are overlaid on the basic magnetic field. A diagram which is used, which describes a chronological sequence of RF pulses to be irradiated and gradients to be switched, is referred to as a pulse sequence (diagram), or also as a sequence for short. The recorded measurement data is digitized and stored as complex numerical values in a k-space matrix. An associated MR image can be reconstructed from the k-space matrix occupied by values, for example by means of a multi-dimensional Fourier transform.

The k-space is frequently sampled on a Cartesian grid, line-by-line along k-space lines running in the readout direction, and a corresponding k-space matrix thus filled line-by-line with values, with, for example, a k-space line being sampled after an excitation. Wrap-around artifacts can develop if a field of view (FoV) recorded in the process does not have adequate coverage.

Wrap-around artifacts of this kind can develop when recording measurement data as a result of the generated echo signals being periodic signals which are recorded as measurement data at discrete k-space points. That is to say therefore, only a certain number of frequencies can be unambiguously acquired (Nyquist Theorem). If, for example, measurement data is recorded for 1,000 k-space points per second, it is possible to acquire frequencies from −500 Hz to +500 Hz. If there are echo signals with higher or lower frequencies, then these likewise appear in the interval −500 Hz to +500 Hz and, more precisely, shifted by a multiple of 1,000 Hz. For example, a signal, which has a frequency of 600 Hz would be acquired in a described measurement as a signal at −400 Hz. This phenomenon is generally referred to as aliasing.

SUMMARY

In order to prevent such wrap-around artifacts and therewith aliasing artifacts, different approaches can be used for different encoding directions.

For instance, if an examination object to be examined goes beyond a selected field of view in the phase-encoding direction, only what is known as oversampling can help. In this connection, the field of view in the image space is selected to be larger than the examination object to be examined (whereby more k-space positions are to be sampled in the affected encoding direction and thus in the phase-encoding direction, for example, more k-space lines are to be sampled). The image obtained is subsequently cut to a smaller field of view again, which contains the examination object to be examined.

If an examination object to be examined goes beyond a selected field of view in the readout direction, a different approach can be selected: before recording the measurement data a band-pass filter can be applied to the received echo signal, which filter suppresses frequencies which are too high and too low, that is to say frequencies which are outside of a field of view band specified by the selected field of view. Simplified, the band-pass filter can be envisaged as a trapezoidal filter in the frequency domain, as is schematically represented in FIG. 1, which in a central plateau c of the trapezoid a lets through all frequencies unaffected, and outside of the trapezoid a completely suppresses all frequencies. The legs of the trapezoid a represent transition bands b in which the filter alternates between letting through and blocking.

Normally, the plateau c is selected such that due to a two-sided extension by a frequency band d of identical breadth in each case, the edges of the plateau c are safely outside of the field of view band freqFoV (c=freqFoV+2*d; d>0), so an attenuation within the transition bands b does not affect a filtered signal within the field of view. Real band-pass filters do not run exactly trapezoidally in the frequency band; rather, the "corners" are more "rounded", so d has to be selected to be sufficiently large that within the field of view band freqFoV the filter does not actually filter a filtered signal.

The frequency band d is selected to be as small as possible because the breadth of the spectrum at frequencies which are still present in a filtered signal is freqFoV+2*d+2*b, and this should be kept as low as possible.

Despite applications of such a band-pass filter, owing to the transition bands b, the spectrum at frequencies in a filtered signal is therefore still larger than the spectrum of the frequencies which come from the field of view FoV, that is to say larger than the spectrum of the field of view band freqFoV. For this reason, in addition to a described band-pass filter, an oversampling can also be carried out in the readout direction. It has become common in this connection to carry out an oversampling with a factor of 2, that is to say to record twice as many data points per unit of time than is actually necessary for one selected according to Nyquist field of view. The factor of 2 is primarily used therefore because even-numbered factors were the easiest to implement with electronic devices available when introducing such a method. It has become common therefore to use a permanently defined oversampling in the readout direction always with a factor of 2 and a permanently defined band-pass filter whose transition bands b are selected in the interval of frequency bands d, which are always identical to the boundary frequencies of the field of view band freqFoV against wrap-around artifacts.

It should be noted that an oversampling in the readout direction does not require any additional time, although it does in the phase-encoding direction since in the phase-encoding direction each further k-space point to be sampled requires a new recording of measurement data, for example along a further k-space line. A band-pass filter thus cannot be used in the phase-encoding direction either, just where in this encoding direction a received echo signal is determined in a large number of individual measurements.

Data obtained during the course of an oversampling is always discarded in the image space, so the desired data from the field of view is cleanly separated from data, which is not required, outside of the field of view. This is not possible in the k-space, since there desired image data and image data which is not required overlaps in all measuring points. However, since a k-space recorded with an oversampling with a factor of 2 also requires twice as much computing capacity, as a rule data of this kind, i.e. recorded by way of an oversampling to prevent wrap-around artifacts (but which is not required in the image space), is discarded very early before, for example, more computing-intensive steps of a final reconstruction of image data are carried out, for instance during the course of simultaneous imaging, or during the course of a coil combination, etc.

The gradient fields used for the spatial encoding when recording measurement data by means of magnetic resonance should ideally be generated such that an optimally accurate linearity, that is to say a linear field behavior, is given while the basic magnetic field should be optimally homogeneous.

However, imperfections can occur in the gradient fields, which can be caused, for example, by the existing nature of the gradient coils of a gradient unit and result in a deviation from the ideal linearity. As a rule, deviations of this kind and accompanying non-linearities of the gradient fields of the gradient unit occur in boundary regions of a measurement volume of a magnetic resonance system. They can also be purposefully permitted when the gradient coils of a gradient unit are developed, for example to make the gradient coils of the gradient unit particularly thin, quiet, and/or inexpensive. As a result of these non-linearities, the slopes of the gradient fields can be steeper or shallower than assumed with the assumption of an existing linearity at a given location in the measurement volume of the magnetic resonance system which comprises the gradient unit. However, when planning the recording of measurement data in a field of view, it is precisely linear gradients that are assumed. Consequently, a slightly different spatial region than the planned field of view is actually encoded.

These kinds of non-linearities of a gradient unit can therefore result in distortions, for example extensions and/or compressions, in the spatial encoding, which usually occur in outer regions of MR images reconstructed from measurement data recorded in this way and which depend on the gradient unit used (e.g. the type of gradient coils) or their distortion characteristics and also on the measurement protocol used when recording the measurement data (e.g. the pulse sequence used).

By way of what are known as distortion corrections, it is possible to eliminate the non-linearities with the aid of stored items of distortion information, e.g. a distortion map, by way of image-based shifts of the corresponding image points. For example, it is known to perform a calibration measurement using a phantom whose geometry is known at least in respect of some marker points to determine a distortion map in respect of the non-linearity of the gradient fields of the gradient unit for a specific magnetic resonance system. A distortion map of this kind can describe distortion coefficients, which establish how a certain image point is to be shifted to rectify the distortion by way of a shift which is opposed to a distortion caused by the non-linearity of the gradients. Distortion corrections of this kind can be applied in two-dimensional (2D) MR image data sets and in three-dimensional (3D) MR image data sets.

For all regions in a distortion-corrected image in which the distortion correction shifts image points inwards, regions form at the boundary of the image in which no measurement data is present, since it has to come from outside of the measured image. This effect of seemingly "cut-off" boundary regions in the image is called cropping.

Even the planning (location and position of the region of interest of an examination object, also called field of view (FoV)) of MR measurements to be carried out is usually carried out on distortion-corrected planning images, also called MR reference images or localizers. Planning on distortion-corrected MR images has many advantages, such as that distortions caused by the non-linearities of the gradient unit cannot be seen in the distortion-corrected MR image, so in the distortion-corrected MR image distances, for example, can be determined distortion-free. Furthermore, when non-distortion-corrected MR images are used for planning after a (frequently necessary) movement of the couch of the magnetic resonance system between planning and execution of the measurement, a new MR reference image has to be recorded to be able to display the distortions applicable to the new position of the couch.

One problem here is that, as described, depending on the direction of the shift in image points, which takes place during the course of the distortion correction, a reduction can occur in the field of view which is actually set, usually defined as a rectangle or cuboid. As stated, this is because recording of the measurement data is carried out during measurement with the non-linear gradient fields of the gradient unit and can thus cover a different region of the examination object than the planning, e.g. on planning images which are themselves already distortion-corrected, would lead one to expect. The situation can thus occur that, owing to the distortion, no measurement data is acquired from specific regions, e.g. at the boundary, of MR images during the recording planned in this way. These regions are thus not mapped since no information exists in the acquired measurement data for these unmapped regions.

It is precisely with off-center measurements, that is to say recordings of measurement data outside of the center of the homogeneity region of the basic magnetic field of the magnetic resonance system used, and therewith in boundary regions of the homogeneity volume of the basic magnetic field, but also, for example, in more modern, rather open and freely designed magnetic resonance systems, that this problem is more pronounced, so cropping effects occur.

As a rule, cropping effects of this kind cannot be corrected despite an oversampling which has potentially already been carried out against aliasing effects since, owing to the otherwise excessive computing effort, the data from the oversampling is discarded even before the image reconstruction and therefore, as described, is missing in affected boundary regions. It is therefore common practice in the case of off-center measurements, for example at the boundary of the bore of the magnetic resonance system, for the user to select the field of view to be larger than is actually necessary, so the regions which cannot be represented, possibly due to cropping effects, do not include any anatomy or no relevant anatomy. However, adequate experience of the user is necessary in this case to select the field of view to be large enough, but also not larger than necessary, to be able to represent everything that is relevant with adequate resolution and in an acceptable measurement time.

The disclosure is based on the object of preventing cropping effects and to make representation of all desired regions, e.g. in the case of off-center measurements, possible, so high-quality MR images with few artifacts can be obtained with the least possible computing effort and the shortest possible measurement time.

The object is achieved by the various embodiments as discussed herein, including those described in the claims.

A method for improved recording of measurement data from a mapping area of an examination object situated in a measurement volume of a magnetic resonance system, comprises the following steps:

loading non-linearity data describing a non-linearity of a gradient unit of the magnetic resonance system, displaying, for example on a user interface of the magnetic resonance system, at least one planning image of an examination object situated in a measurement volume of the magnetic resonance system, selecting a desired field of view in the at least one planning image, loading a measurement protocol which is to be used for recording the measurement data and which comprises gradients to be switched and RF pulses to be irradiated, which trigger echo signals which are received for recording the measurement data, determining at least one loss factor on the basis of the non-linearity data and on the basis of the desired field of view, wherein the at least one loss factor indicates an expected reduction of an image reconstructed on the basis of measurement data recorded with the loaded measurement protocol, determining filter parameters for a frequency filter for filtering frequencies of echo signals, received when recording measurement data with the measurement protocol, on the basis of the loss factor and on the basis of the desired field of view, determining an oversampling factor on the basis of specific filter parameters of the frequency filter, wherein the oversampling factor specifies an oversampling (according to Nyquist) to be applied when recording measurement data, recording oversampled measurement data by carrying out the loaded measurement protocol in the selected field of view using the filter parameters and the oversampling factor.

The selection of filter parameters for a frequency filter for filtering frequencies of echo signals received when recording measurement data with the measurement protocol on the basis of a loss factor determined for the magnetic resonance system used and on the basis of the desired field of view determines a frequency filter which is optimized for an envisaged recording of measurement data. An oversampling factor determined on the basis of optimized filter parameters of this kind is itself likewise optimized for an envisaged recording of measurement data in this case. Using such an optimized frequency filter and such an optimized oversampling factor can ensure that a desired field of view is fully recorded despite non-linearities in a gradient unit of the magnetic resonance system which is used when recording measurement data, with aliasing artifacts being prevented. The method thus makes it possible to prevent cropping effects and aliasing artifacts without a user having to take action, for example in order to select an oversampling factor themselves, with required recording times for the measurement data and reconstruction times for image data from the recorded measurement data not having to be increased, or at most having to be increased slightly, with respect to previous methods.

Non-linearity data describing a non-linearity of a gradient unit of the magnetic resonance system can be loaded in the form of a distortion map.

The distortion map, at least with regard to the imperfections of the gradient fields, is to be regarded as magnetic resonance facility-specific, which means a distortion map ascertained, for example, on the basis of a calibration is known and exists in a storage means of the control facility. Knowledge about which shifts in location actually occur, which is used during the course of the distortion correction, is thereby also known. One idea underlying the disclosure is accordingly to use this knowledge of the distortion map as early as in preparation for a magnetic resonance recording in order to make it possible to determine optimized filter parameters of a frequency filter and an optimized oversampling factor with which measurement data is recorded.

A magnetic resonance system comprises a magnet unit, a gradient unit, a radio-frequency unit and a control facility, embodied to carry out a method, with a filter parameter-determining unit.

A computer program implements a method on a control facility when it is executed on the control facility.

The computer program can also be in the form of a computer program product, which can be loaded directly into a memory of a control facility, with program code means to carry out any of the methods described herein when the computer program product is executed in the computing unit of the computing system.

An electronically readable data carrier comprises electronically readable items of control information saved thereon which comprise at least one computer program and are configured in such a way that they carry out any of the methods described herein when the data carrier is used in a control facility of a magnetic resonance system.

The advantages and statements disclosed in relation to any of the methods described herein also apply analogously to the magnetic resonance system, the computer program product, and the electronically readable data carrier.

BRIEF DESCRIPTION OF THE DRAWINGS

Further advantages and details of the present disclosure can be found in the exemplary embodiments described below as well as on the basis of the drawings. The examples mentioned do not represent any limitation of the disclosure. In the drawings.

DETAILED DESCRIPTION OF THE DISCLOSURE

Figure 2:
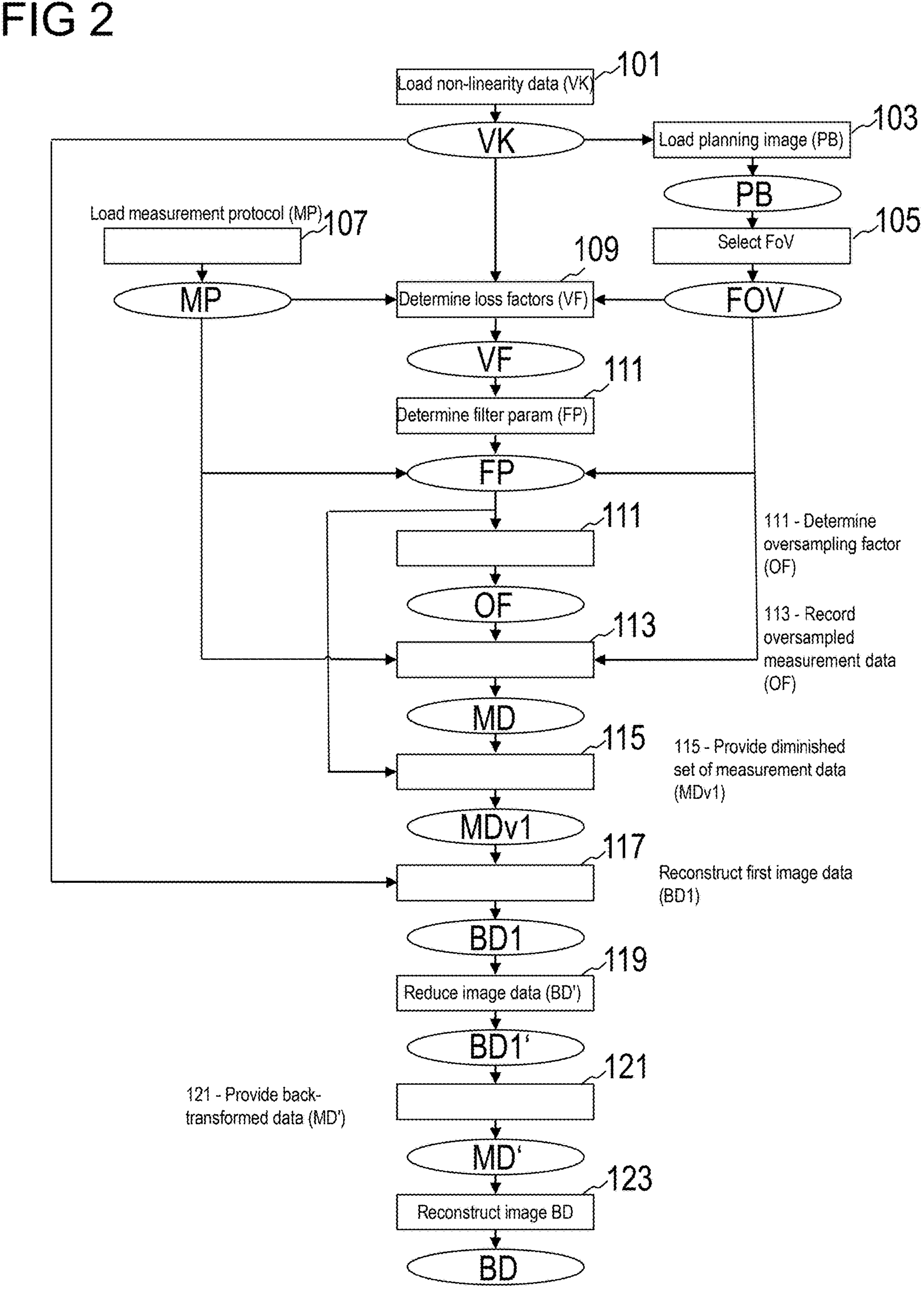
FIG. 2 illustrates a flowchart of an example method, in accordance with the disclosure.

FIG. 2 illustrates a flowchart of an example method, in accordance with the disclosure. More specifically, FIG. 2 is a schematic flowchart of an example method for improved recording of measurement data MD from a mapping area of an examination object U situated in a measurement volume of a magnetic resonance system 1.

Non-linearity data VK describing a non-linearity of a gradient unit 5 of the magnetic resonance system 1 is loaded (Block 101). As already mentioned above, the non-linearity data VK can be loaded, for example, in the form of a distortion map known per se. Customarily distortion maps VK of this kind are determined at least during installation of a magnetic resonance system and exist, for example, in a memory of the system.

At least one planning image PB of an examination object U situated in a measurement volume of the magnetic resonance system 1 is loaded (Block 103). As a rule, planning images PB of this kind are recorded before the beginning of a recording of measurement data by means of magnetic resonance to ensure that the measurement data is recorded in a desired, region of interest of the examination object to be examined. The at least one planning image PB can be displayed, for example on a user interface E/A of the magnetic resonance system 1. The planning image PB can be distortion-corrected in this connection also using the loaded non-linearity data VK.

A desired field of view (FoV) is selected in the at least one planning image PB, for example at a user interface E/A of the magnetic resonance system 1 (Block 105). This is a conventional procedure which, as a rule, occurs by way of a user. The method proposed herein is especially recommended if a desired field of view FoV is not centrally located, but "off-center", in the planning image PB and thus an off-center measurement is to be carried out in which, without the method described herein, cropping effects would occur.

A measurement protocol MP to be used to record the measurement data MD and which comprises gradients to be switched and RF pulses to be irradiated, which trigger echo signals which are to be received for recording to record the measurement data MD, is loaded (Block 107). The measurement protocol specifies, e.g. a pulse sequence which is to be used when recording the measurement data and thus specifies how the measurement data is to be recorded and which contrasts are achieved in this connection.

At least one loss factor VF is determined on the basis of the non-linearity data VK and on the basis of the desired FoV, with the at least one loss factor VF indicating an expected reduction of an image reconstructed on the basis of measurement data MD recorded with the loaded measurement protocol MP (Block 109).

A specific loss factor VF can indicate, for instance, an expected reduction of an image reconstructed on the basis of recorded measurement data MD in the readout direction. As described above, a frequency filter and/or oversampling can advantageously be used against artifacts in the readout direction.

The at least one loss factor VF can be a "left-handed loss factor", which indicates an expected reduction on the left-hand side of the image, and/or a "right-hand loss factor", which indicates an expected reduction on the right-hand side of the image. Generally, local loss factors VF can be determined from the non-linearity data VK in accordance with the local non-linearities which exist in accordance with the non-linearity data VK. As a rule, the boundary regions of images recorded by means of MR are affected the most by non-linearities of the gradients, so loss factors can be determined at least for the left-hand and/or right-hand boundary of the image. Depending on the location of the field of view FoV, it is also possible to determine only a left-hand or a right-hand loss factor, for example if reductions are to be expected only at the left-hand or right-hand boundary of the image due to the prevailing non-linearities of the gradients.

Filter parameters (FP) are determined on the basis of the at least one loss factor VF and on the basis of the desired field of view FoV for a frequency filter for filtering frequencies of echo signals received when recording measurement data MD with the measurement protocol MP (Block 111).

Figure 1:
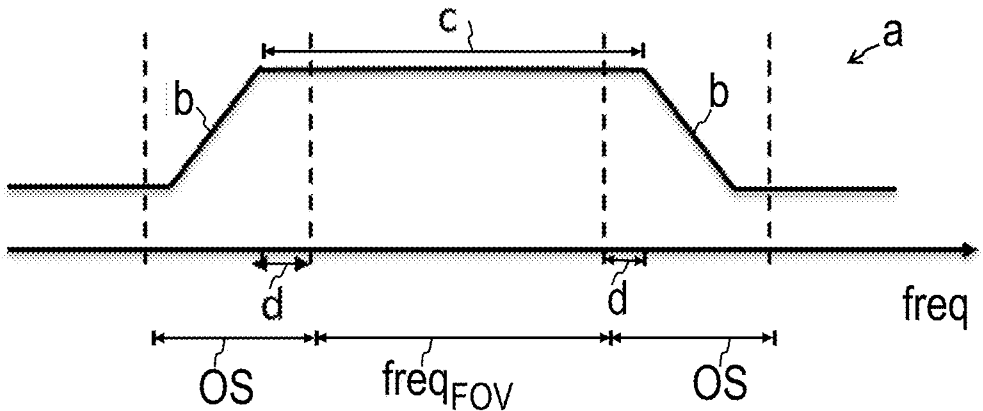
FIG. 1 illustrates a representation of an example frequency filter, in accordance with the disclosure.

The basis for the frequency filter can be a trapezoidal band-pass filter described in accordance with FIG. 1 for instance, so the filter parameters define, for example, a stopband, a passband and transition bands of the frequency filter. In the present method, the passband will comprise a field of view band (freqFoV) dependent on the desired field of view FoV, and at least one extension band d determined on the basis of the loss factor VF. The at least one extension band d thus depends on a respective at least one loss factor VF, which was determined on the basis of the non-linearity data VK of the magnetic resonance system 1 and the field of view FoV and is thus specific to both the planned recording of measurement data MD and to the magnetic resonance system 1 used and is thus particularly effective against cropping effects. As a rule, the transition bands are dependent on the filter hardware which is used and are thus selected to be as small as possible. The stopband then results as those frequencies which are not in a transition band or in the passband.

An extension band d can be determined, for example, in such a way that the extension band d is located directly next to the field of view band, that is to say the frequencies of the extension band d directly connect to the frequencies of the field of view band freqFoV, and a breadth of the extension band d corresponds to a multiple of the field of view band freqFoV corresponding to the loss factor VF. If the determination of the loss factor produces, for example, a reduction by 25%, that is to say that due to the non-linearities, without further measures 25% of the image would be lost, the breadth of the extension band d is set to 25% of the field of view band freqFoV. The passband of the frequency filter can then be widened on both sides of the field of view band freqFoV by the breadth of the extension band d, so the passband to the left and right of the field of view band freqFoV is widened by the breadth of an extension band d. This ensures that there is an adequate signal available in the passband for a subsequent distortion correction.

However, it is also conceivable that in each case one separate extension band d on the left is determined on the basis of a "left-hand" loss factor VF and one extension band d on the right is determined on the basis of a "right-hand" loss factor VF, in each case next to the field of view band freqFoV, so the passband then comprises the left-hand extension band d, the field of view band freqFoV and the right-hand extension band d. An extension band d, which is associated with a boundary of a field of view FOV at the boundary of the bore of the magnetic resonance system, is greater than an extension band d, which is associated with a boundary of a field of view FoV closer to the center of the bore of the magnetic resonance system, with it also being possible for the latter to be negligibly small.

An oversampling factor OF, which specifies an oversampling (according to Nyquist) to be applied when recording measurement data, is determined on the basis of at least one specific filter parameter FP of the frequency filter (Block 111). The oversampling factor OF thus determines an oversampling which is to be applied. The oversampling and therewith the oversampling factor should be as large as necessary to cover, for example, the complete breadth of a frequency filter, that is to say its passband and possible transition bands, but should be kept as small as possible to prevent unnecessary recording of measurement data. In modern analog-digital converters or other filtering facilities of a magnetic resonance system 1, random values can also be set without problems to be greater than two for oversampling factors OF in order to prevent aliasing artifacts.

The oversampling factor OF can also be optimally determined from the optimally determined filter parameters of the frequency filter, for example by determining the oversampling factor OF as the quotient of the sum of the breadths of a passband of the frequency filter and the breadths of the transition bands of the frequency filter as a dividend and the breadth of a field of view band dependent on the desired field of view as a divisor. In this way, in contrast to previous rigid methods with fixed extension bands d, it is ensured that sufficient (but not too much) measurement data is recorded by oversampling in accordance with the oversampling factor OF.

Oversampled measurement data MD is recorded by implementing the loaded measurement protocol MP in the selected field of view FOV using the filter parameters FP and the oversampling factor OF (Block 113).

A first part of the oversampled measurement data MD determined on the basis of the filter parameters FP of the frequency filter, for example measurement data from frequency bands of the transition bands b of the frequency filter, can be discarded (Block 115), so a diminished set of measurement data MDv1 remains (MDv1). In this way, measurement data which is not necessary for further method steps, which can still remain despite application of the frequency filter, can be removed, whereby further processing is facilitated and accelerated without the quality of the image data that is ultimately obtained suffering.

First image data BD1 can be reconstructed (Block 117) from a diminished set of measurement data MDv1, e.g. by way of a one-dimensional Fourier transform in the readout direction of k-space lines which have already been individually recorded. First image data BD1 of this kind can be distortion-corrected using the loaded non-linearity data VK, so the first image data BD1 is distortion-corrected. Since the first image data BD1 has already been reconstructed from a diminished set of measurement data MDv1, the distortion correction thereof requires less effort. Distortions in the image data caused by the non-linearities of the gradients can be corrected by the distortion correction.

In the possibly distortion-corrected first image data BD1, only data recorded owing to the oversampling factor OF used can be discarded, so reduced first image data BD1' remains (Block 119).

This kind of discarding of "too much" recorded data can be carried out as described above by determining in the image space the data which can be discarded since it was recorded solely by oversampling in the extension bands d in order to prevent wrap-around artifacts. In this way, measurement data recorded by way of the extension bands d only to prevent artifacts can be discarded in the image space, so reduced first image data BD1' is obtained.

The reduced (possibly distortion-corrected) first image data BD1' can be transformed back into the frequency domain of the measurement data, so back-transformed, reduced measurement data MD' is obtained (Block 121). Due to the discarding of measurement data carried out in Blocks 115 and 119, the back-transformed, reduced measurement data MD' no longer contains any measurement data which was recorded only in order to prevent adverse effects such as cropping, wrap-around artifacts and aliasing artifacts, which would otherwise significantly slow down and/or impair more complex and more computing-intensive reconstructions.

An image BD of the mapping area can be reconstructed (Block 123) from the back-transformed reduced measurement data MD', which image is free from cropping effects and aliasing artifacts.

Figure 3:
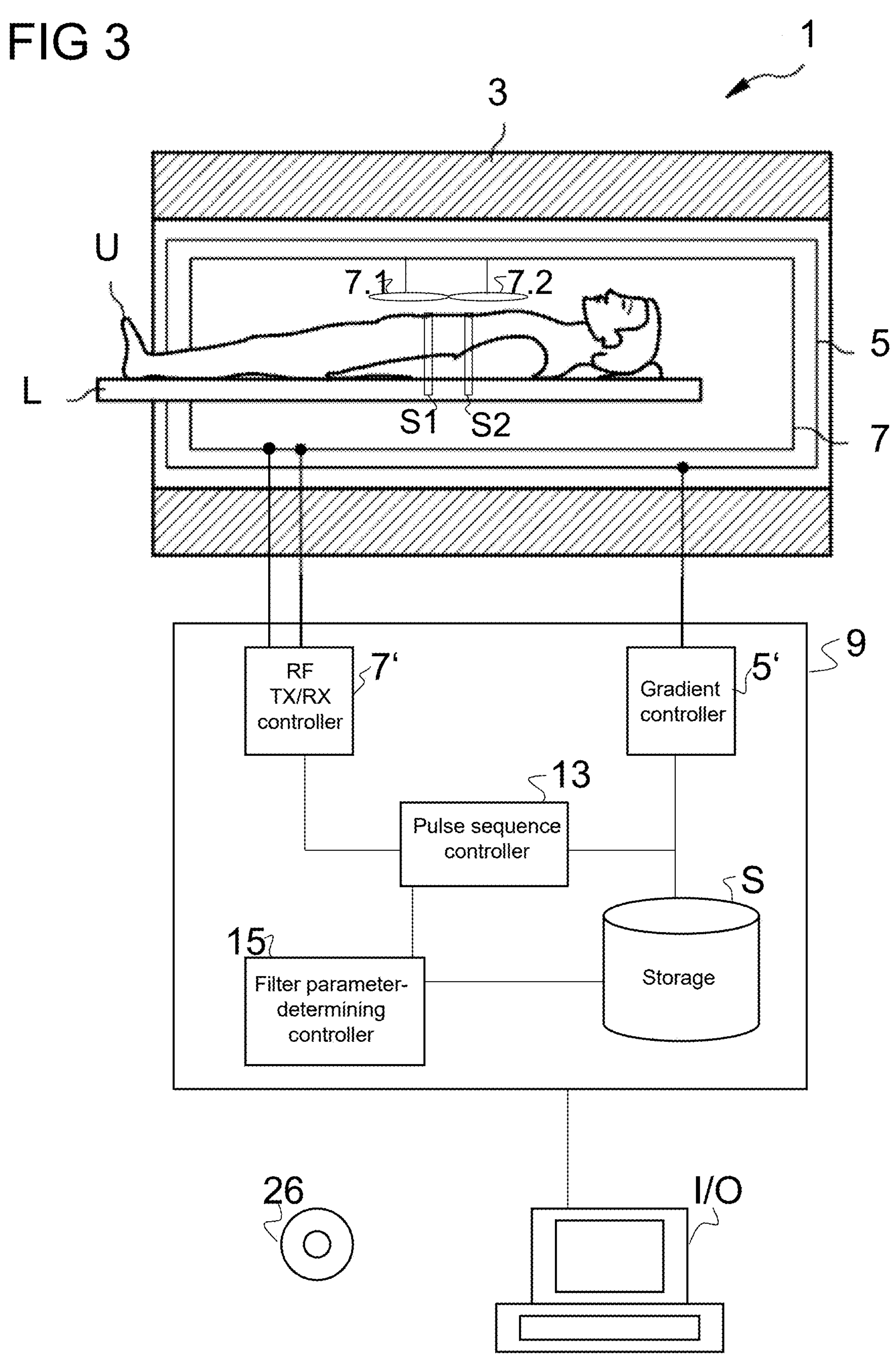
FIG. 3 illustrates an example magnetic resonance system, in accordance with the disclosure.

FIG. 3 illustrates an example magnetic resonance system, in accordance with the disclosure. More specifically, FIG. 3 schematically represents a magnetic resonance system 1. This comprises a magnet unit 3 (also referred to herein as a main magnet) for generating the basic magnetic field, a gradient unit 5 (also referred to herein as a gradient generation circuitry or gradient coils) for generating the gradient fields, a radio-frequency unit 7 (also referred to herein as an RF transmitter, receiver, or transceiver) for irradiating and receiving radio-frequency signals and a control facility 9 (also referred to herein as a controller) embodied to carry out any of the methods as described herein.

These part units of the magnetic resonance system 1 are only roughly schematically represented in FIG. 3. In an embodiment, the radio-frequency unit 7 can be composed of a plurality of subunits, for example of a plurality of coils like the schematically shown coils 7.1 and 7.2, or more coils which can either be embodied only for sending radio-frequency signals or only for receiving the triggered radio-frequency signals or for both.

To examine an examination object U, for example a patient or also a phantom, it can be introduced on a couch L into the magnetic resonance system 1 in the measurement volume thereof. The slices or slabs S1, S2 represent exemplary (partial) target volumes of the examination object from which echo signals are to be recorded and acquired as measurement data.

The control facility 9 serves to control the magnetic resonance system 1 and can control, for example, the gradient unit 5 by means of a gradient controller 5' and the radio-frequency unit 7 by means of a radio-frequency transmit/receive controller 7'. The radio-frequency unit 7 can comprise a plurality of channels on which signals can be sent or received.

The radio-frequency unit 7, together with its radio-frequency transmit/receive controller 7', is responsible for generating and irradiating (sending) a radio-frequency alternating field for manipulation of the spins in a region to be manipulated (for example in slices S to be measured) of the examination object U. As a rule, the center frequency of the radio-frequency alternating field, also referred to as the B1 field, is optimally set such that it is close to the resonance frequency of the spins to be manipulated. Deviations of the center frequency z from the resonance frequency are referred to as off-resonance. Currents controlled by means of the radio-frequency transmit/receive controller 7' are applied in the radio-frequency unit 7 to the HF coils in order to generate the B1 field.

A pulse sequence unit 13 (also referred to herein as processing circuitry, pulse sequence circuitry, or a pulse sequence controller) incorporated by the control facility 9 is embodied to carry out all computing operations necessary for the necessary measurements and determinations for the calculation of RF pulses to be irradiated and gradients to be switched. Intermediate results and results required for this or ascertained in this connection can be saved in a memory unit S (also referred to herein as storage) of the control facility 9. The represented units are not necessarily to be understood as physically separate units in this case, rather they merely represent a subdivision into units of meaning, but they can also be implemented, for example, in fewer or also in just a single physical unit.

Furthermore, the control facility 9 comprises a filter parameter-determining unit 15 (also referred to herein as processing circuitry, filter parameter-determining circuitry, or a filter parameter-determining controller) with which filter parameters can be determined for an optimized frequency filter for recording measurement data, on the basis of which, for example by means of the pulse sequence unit 13, an optimized oversampling factor can be determined for recording measurement data. The control facility 9 is embodied overall to carry out any of the methods as discussed herein.

Control commands can be passed to the magnetic resonance system and/or results of the control facility 9, such as image data, can be displayed, for example by a user, via a user interface (I/O) of the magnetic resonance system 1 for inputting and outputting data and items of information.

A method described herein can also exist in the form of a computer program product which comprises a program and implements the described method on a control facility 9 when it is executed on the control facility 9. Similarly, an electronically readable data carrier 26 with electronically readable items of control information saved thereon can exist, which items comprise at least one such computer program product as just described and are embodied in such a way that they carry out the described method when the data carrier 26 is used in a control facility 9 of a magnetic resonance system 1.

The various components described herein may be referred to as "units." Such components may be implemented via any suitable combination of hardware and/or software components as applicable and/or known to achieve their intended respective functionality. This may include mechanical and/or electrical components, processors, processing circuitry, or other suitable hardware components, in addition to or instead of those discussed herein. Such components may be configured to operate independently, or configured to execute instructions or computer programs that are stored on a suitable computer-readable medium. Regardless of the particular implementation, such units, as applicable and relevant, may alternatively be referred to herein as "circuitry," "controllers," "processors," or "processing circuitry," or alternatively as noted herein.

What is claimed is:

1. A method for recording measurement data from a mapping area of an examination object situated in a measurement volume of a magnetic resonance system, the method comprising:

loading non-linearity data describing a non-linearity of a gradient unit of the magnetic resonance system;

displaying, on a user interface, a planning image of the examination object situated in the measurement volume of the magnetic resonance system;

selecting a field of view (FoV) in the planning image;

loading a measurement protocol for recording the measurement data, the measurement protocol comprising gradients to be switched and radio frequency (RF) pulses to be irradiated that trigger echo signals for recording the measurement data;

determining a loss factor based on the non-linearity data and the selected FoV, wherein the loss factor indicates an expected reduction of a reconstructed image based on the recorded measurement data;

determining filter parameters for a frequency filter for filtering frequencies of the echo signals based on the loss factor and the FoV;

determining an oversampling factor based on the filter parameters, wherein the oversampling factor specifies an oversampling to be applied when recording the measurement data, and recording oversampled measurement data by executing the loaded measurement protocol in the selected FoV using the filter parameters and the oversampling factor.

2. The method as claimed in claim 1, wherein the non-linearity data is loaded in the form of a distortion map.

3. The method as claimed in claim 1, wherein the loss factor indicates an expected reduction of the reconstructed image based on the measurement data that is recorded with the loaded measurement protocol in a readout direction.

4. The method as claimed in claim 1, wherein the filter parameters define a stopband, a passband, and transition bands of the frequency filter, and wherein the passband comprises a FoV band that is dependent on the selected FoV and an extension band that is determined based on the loss factor.

5. The method as claimed in claim 4, further comprising:

determining the extension band as being located directly next to the FoV band, wherein a breadth of the extension band corresponds to a multiple of the FoV band.

6. The method as claimed in claim 4, wherein determining the extension band comprises determining a respective extension band to a left and right of the FoV band.

7. The method as claimed in claim 1, wherein the oversampling factor is determined as a quotient of a sum of breadths of a passband of the frequency filter and breadths of transition bands of the frequency filter as a dividend, and wherein a breadth of a FoV band is dependent on the selected FoV as a divisor.

8. The method as claimed in claim 1, wherein a first part of the oversampled measurement data is discarded to provide a diminished set of measurement data, and further comprising:

reconstructing, from the diminished set of measurement data, first image data via a one-dimensional Fourier transform in a readout direction.

9. The method as claimed in claim 8, further comprising:

distortion correcting the first image data using the loaded non-linearity data to provide distortion-corrected first image data.

10. The method as claimed in claim 9, wherein in the distortion-corrected first image data, only data recorded owing to the oversampling factor is discarded such that the reduced first image data remains, and further comprising:

transforming the reduced first image data to the frequency domain of the measurement data to obtain back-transformed reduced measurement data; and generating the reconstructed image based upon the back-transformed reduced measurement data.

11. The method as claimed in claim 1, wherein the selected FoV is not centrally located in the planning image.

12. The method as claimed in claim 1, wherein the loss factor comprises (i) a left-handed loss factor that indicates an expected reduction on a left-hand side of the reconstructed image, and/or (ii) a right-handed loss factor that indicates an expected reduction on a right-hand side of the reconstructed image.

13. A magnetic resonance system, comprising:

a magnet unit;

a gradient unit;

a radio frequency (RF) unit; and a control facility including an RF send/receive controller and a filter parameter determining unit, the control facility being configured to record measurement data from a mapping area of an examination object situated in the measurement volume by:

loading non-linearity data describing a non-linearity of the gradient unit of the magnetic resonance system;

displaying, on a user interface, a planning image of the examination object situated in the measurement volume of the magnetic resonance system;

selecting a field of view (FoV) in the planning image;

loading a measurement protocol for recording the measurement data, the measurement protocol comprising gradients to be switched and radio frequency (RF) pulses to be irradiated that trigger echo signals for recording the measurement data;

determining a loss factor based on the non-linearity data and the selected FoV, wherein the loss factor indicates an expected reduction of a reconstructed image based on the recorded measurement data;

determining filter parameters for a frequency filter for filtering frequencies of the echo signals based on the loss factor and the FoV;

determining an oversampling factor based on the filter parameters, wherein the oversampling factor specifies an oversampling to be applied when recording the measurement data, and recording oversampled measurement data by executing the loaded measurement protocol in the selected FoV using the filter parameters and the oversampling factor.

14. A non-transitory computer readable medium having instructions stored thereon that, when executed by a controller of a magnetic resonance system, cause the magnetic resonance system to record measurement data from a mapping area of an examination object situated in a measurement volume of the magnetic resonance system by:

loading non-linearity data describing a non-linearity of a gradient unit of the magnetic resonance system;

displaying, on a user interface, a planning image of the examination object situated in the measurement volume of the magnetic resonance system;

selecting a field of view (FoV) in the planning image;

loading a measurement protocol for recording the measurement data, the measurement protocol comprising gradients to be switched and radio frequency (RF) pulses to be irradiated that trigger echo signals for recording the measurement data;

determining a loss factor based on the non-linearity data and the selected FoV, wherein the loss factor indicates an expected reduction of a reconstructed image based on the recorded measurement data;

determining filter parameters for a frequency filter for filtering frequencies of the echo signals based on the loss factor and the FoV;

determining an oversampling factor based on the filter parameters, wherein the oversampling factor specifies an oversampling to be applied when recording the measurement data, and recording oversampled measurement data by executing the loaded measurement protocol in the selected FoV using the filter parameters and the oversampling factor.

* * * * *